United States Patent [19]
Lee

[11] Patent Number: 5,657,118
[45] Date of Patent: Aug. 12, 1997

[54] DEVICE AND METHOD FOR DETECTION/MEASUREMENT OF LIGHT

[76] Inventor: John T. S. Lee, 107 Midsummer Dr., Gaithersburg, Md. 20878

[21] Appl. No.: 589,991

[22] Filed: Jan. 23, 1996

[51] Int. Cl.⁶ .............................. G01N 1/10; G01N 21/01
[52] U.S. Cl. .................................... 356/246; 356/244
[58] Field of Search ........................ 356/246, 244; 250/361; 436/172, 47; 422/63–67, 73, 100, 102, 104

[56] References Cited

U.S. PATENT DOCUMENTS

| | | | |
|---|---|---|---|
| 4,003,151 | 1/1977 | Tolosa et al. | 40/106.1 |
| 4,004,150 | 1/1977 | Natelson | 250/328 |
| 4,090,789 | 5/1978 | Macemon et al. | 356/85 |
| 4,154,795 | 5/1979 | Thorne | 422/99 |
| 4,501,970 | 2/1985 | Nelson | 250/458.1 |
| 4,580,895 | 4/1986 | Patel | 356/39 |
| 4,755,055 | 7/1988 | Johnson et al. | 356/440 |
| 4,772,453 | 9/1988 | Lisenbee | 422/52 |
| 4,802,768 | 2/1989 | Gifford et al. | 356/417 |
| 4,818,883 | 4/1989 | Anderson et al. | 250/361 |
| 4,979,821 | 12/1990 | Schutt et al. | 356/246 |
| 5,071,625 | 12/1991 | Kelln et al. | 422/72 |
| 5,082,628 | 1/1992 | Andreotti et al. | 422/82.08 |
| 5,086,233 | 2/1992 | Stafford et al. | 250/576 |
| 5,096,670 | 3/1992 | Harris et al. | 422/65 |
| 5,139,745 | 8/1992 | Barr et al. | 422/82.05 |
| 5,192,510 | 3/1993 | Zoha et al. | 422/82.05 |
| 5,202,091 | 4/1993 | Lisenbee | 422/52 |
| 5,290,513 | 3/1994 | Berthold et al. | 422/52 |
| 5,321,261 | 6/1994 | Valenta | 250/252.1 |
| 5,401,465 | 3/1995 | Smethers et al. | 422/63 |
| 5,445,794 | 8/1995 | Wihlborg | 422/52 |

Primary Examiner—Frank G. Font
Assistant Examiner—Michael P. Stafira
Attorney, Agent, or Firm—Wigman, Cohen, Leitner & Myers, P.C.

[57] ABSTRACT

A device and method for the detection of light emitted by chemically reactive substances is disclosed. The device comprises a plurality of wells for holding chemically reactive substances, a detector for detecting light emitted by the chemically reactive substances held in each well, and a moving component for moving the detector sequentially to each respective one of a series of detection positions, proximate to each well, so as to enable the detector to detect the light emitted by the chemically reactive substance in each well. The detector employed in the present invention comprises a photomultiplier tube and, in accordance with the invention, a processor is employed to control the gain of the photomultiplier tube.

20 Claims, 5 Drawing Sheets

DEVICE AND METHOD FOR DETECTION/ MEASUREMENT OF LIGHT

TECHNICAL FIELD

The present invention generally relates to a device and method for the detection and measurement of light, and more particularly a device and method for the detection of light emitted by chemically reactive substances held in a plurality of wells.

BACKGROUND ART

It is well known, in the art of luminescence detection and measurement, that certain substances undergo a chemical reaction which results in the emission of luminescence or light from those substances. This phenomenon is the basis for analysis in clinical and research laboratories.

For example, the detection and measurement of luminescence forms the basis for such processes as luminescence innumo assay (LIA), in that bioluminescent and chemiluminescent reactions are utilized in such assays.

In such procedures, typically, the luminescent or light-emitting substances are deposited in a plurality of wells, and a detector having a fixed detector position is provided. In order to detect the light emitted from the chemically reactive substances in the wells, the array of wells is typically moved in accordance with a predetermined pattern so that each successive well is moved into the detection position. In this manner, detection data are obtained from each substance in each successive well.

Such a technique and arrangement are disclosed, for example, in U.S. Pat. No. 4,772,453—Lisenbee and U.S. Pat. No. 5,202,091—Lisenbee. However, there are problems and disadvantages associated with the arrangement described above and disclosed in the latter patents.

A primary disadvantage of arrangements of the prior art resides in the fact that, due to the bulky nature of the detection device and associated circuitry, the detector and its associated circuitry are maintained in a fixed detection position, and the plurality of wells in which the substances are contained is moved in accordance with a predetermined pattern of movement. This movement can result in disturbance of the substances contained in the wells and, in an extreme case, could result in spillage of those substances. In addition, such an arrangement of the prior art is necessarily inflexible in that the plurality of wells is moved in one, and only one, predetermined pattern of movement.

Furthermore, in such arrangements of the prior art, the detection device typically employed is a photomultiplier tube (PMT). In order to obtain satisfactory test results, an adjustable aperture is employed between the PMT and the plurality of wells. Moreover, it is necessary, during operation of such an arrangement of the prior art, to physically adjust the aperture size. Moreover, even if it is possible to electronically control or adjust the size of the aperture associated with the PMT, such adjustment is relatively slow and unreliable in that physical movement of the aperture is necessary.

Therefore, there is a need in the prior art for a device and method for detection of light emitted by chemically reactive substances held in a plurality of wells, wherein the detector and its associated circuitry are moved relative to the wells, rather than vice-versa. In addition, there is a need in the prior art for the development of a device and method for detection of light emitted by chemically reactive substances, wherein the slow and relatively less reliable technique of adjusting the size of the aperture associated with a PMT detector is replaced by a quicker and more reliable technique.

Other arrangements representative of the prior art are disclosed in the following U.S. Pat. Nos. 4,154,795; 4,501,970; 4,580,895; 4,755,055; 4,818,883; 5,082,628; 5,086,233; 5,139,745; 5,321,261; and 5,401,465.

DISCLOSURE OF INVENTION

The present invention generally relates to a device and method for detection of light emitted by chemically reactive substances, and more particularly to a device and method for detection of light emitted by chemically reactive substances held in a plurality of wells.

In accordance with the present invention, a device for the detection of light emitted by chemically reactive substances held in a plurality of wells comprises a detector and associated circuitry for detecting the light emitted by the chemically reactive substances held in each well when the detector is positioned in a respective detection position proximate to each well, and a moving component for moving the detector and its associated circuitry sequentially to each respective detection position associated with each well so as to enable the detector to detect the light emitted by the chemically reactive substance contained in that well.

In accordance with a preferred embodiment of the invention, movement of the detector is controlled by a processor or central processing unit (CPU) which generates movement control signals (for example, X-movement and Y-movement control signals) so as to move the detector in a predetermined pattern relative to the plurality of wells. In addition, in a preferred embodiment of the invention, the processor or CPU not only receives the detection data and processes same, but also generates a gain control signal which controls the gain of the PMT detector. The latter characteristic is a quicker and more reliable technique for controlling the operation of the PMT detector, as contrasted with the technique of the prior art (discussed above) wherein the physical size of an aperture associated with the PMT detector is controlled or adjusted, either physically/mechanically or electronically.

Therefore, it is a primary object of the present invention to provide a device and method for the detection of light emitted by chemically reactive substances held in a plurality of wells.

It is an additional object of the present invention to provide a device and method for the detection of light emitted by chemically reactive substances, wherein the detector and its associated circuitry are moved relative to the plurality of wells.

It is an additional object of the present invention to provide a device and method for the detection of light emitted by chemically reactive substances, wherein the detector and its associated circuitry are moved in accordance with a predetermined pattern relative to an array of wells arranged in columns and rows.

It is an additional object of the present invention to provide a device and method for the detection of light emitted by chemically reactive substances, wherein a PMT is employed as the detector.

It is an additional object of the present invention to provide device and method for the detection of light emitted by chemically reactive substances utilizing a PMT, the gain of which is controlled by a processor or CPU.

The above and other objects, and the nature of the invention, will be more clearly understood by reference to the following detailed description, the appended claims, and the accompanying drawings.

BEST MODE FOR CARRYING OUT THE INVENTION

The invention will now be described in more detail with references to the various figures of the drawings.

Figure 1:
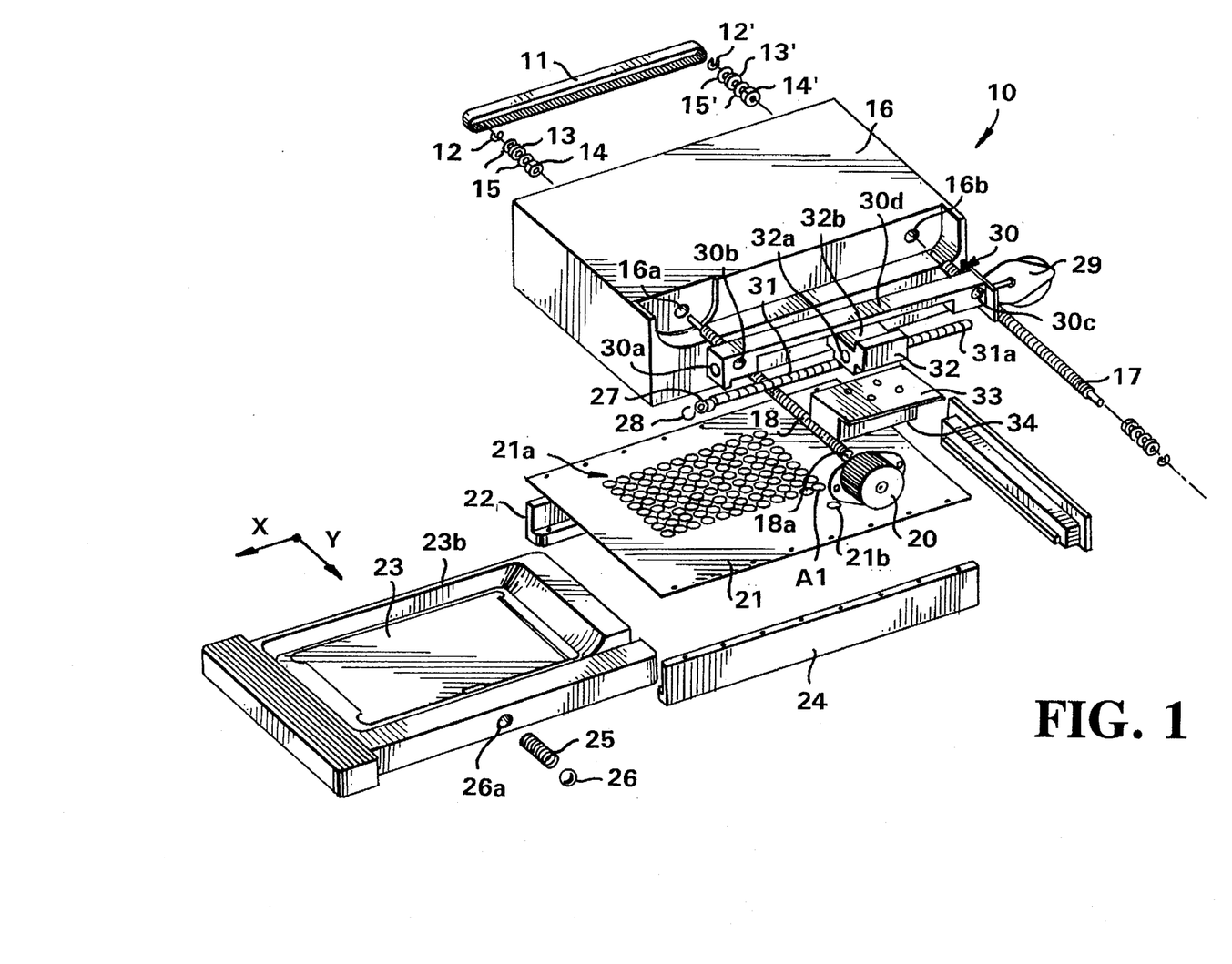
FIG. 1 is a perspective view of the device of the present invention.

FIG. 1 is a perspective view of the device of the present invention. As seen therein, the detection/measurement device 10 comprises the following primary elements: drive belt 11, main body 16, Y-axis parallel screw 17, Y-axis drive screw 18, Y-axis stepping motor 20, mask plate 21, sample tray 23, X-axis stepping motor 29, X-axis carrier 30, X-axis drive screw 31, PMT electronics carrier block 32, PMT electronics circuit board 33, and PMT unit 34.

During usage of the device 10, a plurality of individual wells is established by superimposing mask plate 21 on sample tray 23, the tray 23 having a plurality of individual cells or wells (not shown) formed therein and arranged in rows and columns corresponding to an array of holes 21 a arranged in mask plate 21. Sample tray 23 is mounted between left side rail 22 and right side rail 24. A ball detent spring 25 and detent ball 26 are inserted into the recess 26a provided in the side of tray 23. The spring 25 and ball 26 serve to latch the tray 23 in position between rails 22 and 24. Specifically, a further detent (not shown) is provided on the inner surface of rail 24 so that, when the tray 23 is slid into position between rails 22 and 24, the spring-motivated ball 26 come to rest in the detent (not shown) in rail 24, thereby latching the tray 23 in position between rails 22 and 24.

The device 10 is further assembled by passing X-axis drive screw 31 through the hole 30a in X-axis carrier 30, and through the matching hole 32a in PMT electronics carrier block 32, and then through a further matching hole (not shown) in the end of carrier 30 adjacent to X-axis stepping motor 29, so that the distal end 31 a of drive screw 31 comes to rest in the motor 29. A ball bearing 27 is positioned on the left end of drive screw 31 (as seen in FIG. 1), and the ball bearing 27 is locked in place by inner retaining ring 28. The latter facilitates rotation of drive screw 31 as mounted in carrier 30 and as driven by motor 29.

It should be noted that, in accordance with the present invention, the hole 32a passing horizontally through block 32 is internally threaded, and that the external surface of drive screw 31 is also threaded, so that rotation of drive screw 31 by motor 29 causes horizontal movement of block 32 along the axis of drive screw 31 (defined as the X-axis or X-direction).

The device 10 of the present invention is further assembled by inserting the X-carrier 30 into the interior of main body 16, and passing Y-axis drive screw 18 through the hole 16a provided in main body 16 and through a matching hole 30b provided in one end of carrier 30. Drive screw 18 then emerges from main body 16 through a further hole (not shown) in the rear surface thereof, and a pulley 13 is mounted on the distal end of drive screw 18 by use of nylon flanges 15 and retaining ring 12. A ball bearing 14 is, preferably, also mounted on the distal end of drive screw 18 so as to provide easy rotation of drive screw 18 within the main body 16 of the device 10. Finally, the near or proximate end 18a of drive screw 18 is mounted in Y-axis stepping motor 20 so that the drive screw 18 is driven by the motor 20.

Similarly, Y-axis parallel screw 17 is passed through the hole 16b in main body 16, and through a matching hole 30c provided in carrier 30. Parallel screw 17 emerges from main body 16 through a hole (not shown) in the rear surface of main body 16, and a pulley 13' is mounted on the distal end of parallel screw 17 by use of retaining ring 12' and nylon flanges 15'. A ball bearing 14' is, preferably, mounted on the distal end of parallel screw 17 so as to facilitate its rotation.

Finally, a drive belt 11 is mounted on pulleys 13 and 13' so as to mechanically link drive screw 18 and parallel screw 17. As a result, when the drive screw 18 is driven by stepping motor 20 in a given direction, drive belt 11 rotates in that direction, and accordingly parallel screw 17 also rotates in that direction. Moreover, in accordance with the present invention, the external surfaces of drive screw 18 and parallel screw 17 are threaded, and the holes or passages 30b and 30c provided in the carrier 30 are internally threaded, so that, when stepping motor 20 rotates drive screw 18 in a given direction, the movement of drive screw 18 and corresponding movement of parallel screw 17 cause the carrier 30 to move horizontally in a direction parallel to the axes of screws 17 and 18 (that is, in a direction designated as the Y-axis or Y-direction).

Electronics carrier block 32 has a groove 32b provided in its upper surface so that, when the device 10 is assembled, the groove 32b of block 32 has a matching engagement with the central portion 30d of carrier 30. Accordingly, carrier block 32 can move in only one direction, that is, in the X-direction or along the length of X-axis carrier 30.

PMT electronics circuit board 33 and PMT unit 34 are mounted to a bottom portion of carrier block 32 so that, as carrier block 32 moves in the X and Y directions, the PMT electronic circuit board 33 and PMT unit 34 move correspondingly.

In operation, X-axis stepping motor 29 is activated in a manner to be described below so as to move the PMT unit 34 (which contains a detector unit described below) in the X-direction from one well to another, that is, along a given row of wells. When the unit 34 reaches the end of a given row of wells, the Y-axis stepping motor 20 is activated to move the unit 34 a given distance in the Y-direction so as to align the unit 34 with the next row of wells. Then, the X-axis stepping motor 29 is activated to move the unit 34 from one well to another in the next row of wells. The process continues in this manner until all wells in a given row and all rows in the array of wells 21 a have been subjected to detection by the unit 34.

Figure 2:
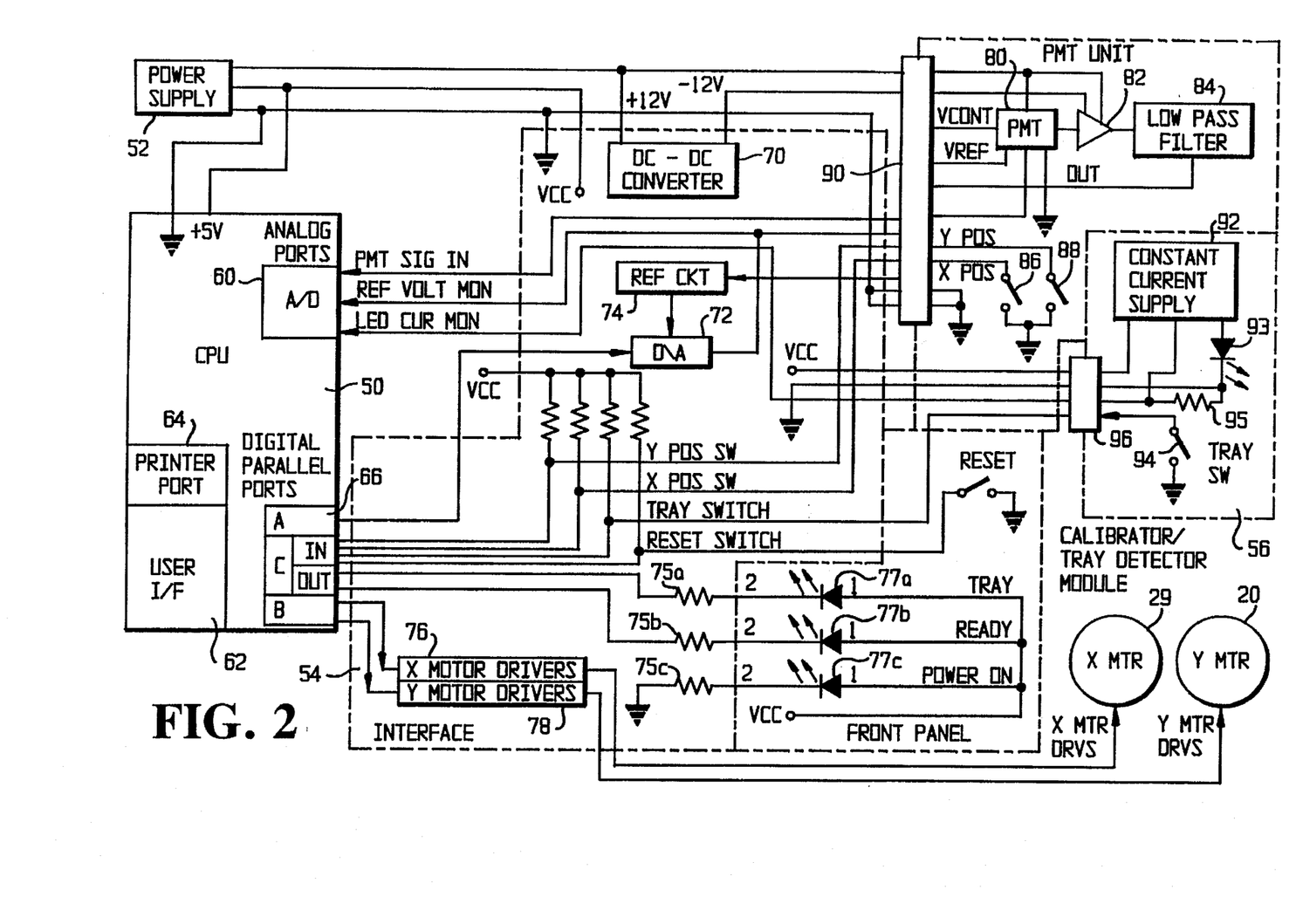
FIG. 2 is a functional block diagram of the present invention.

FIG. 2 is a functional block diagram of the device of the present invention. As seen therein, the present invention basically comprises a central processing unit (CPU) 50 powered by a power supply 52, and connected via an interface 54 to a PMT unit 34 and to a calibrator/tray detector module 56. In particular, PMT unit 34 and calibrator/tray detector module 56 are connected to interface 54 and other components by conventional connectors 90 and 96, respectively.

The CPU 50 comprises analog-to-digital (A/D) converter 60, user interface 62, printer port 64, and digital parallel ports 66 (specifically, A, B, C IN and C OUT ports).

Interface 54 comprises DC—DC converter 70, digital-to-analog (D/A) converter 72, reference circuit 74, X motor drivers 76 and Y motor drivers 78. The drivers 76 and 78 are connected to X motor 29 and Y motor 20, respectively.

PMT unit 34, comprises PMT 80, amplifier 82, low pass filter 84, X-position switch 86, and Y-position switch 88. The PMT 80 and amplifier 82 receive direct current (DC) voltage from power supply 52 via connector 90.

Finally, calibrator/tray detector module 56 comprises constant current supply 92, LED 93, tray switch 94, and resistor 95.

The operation of the device of the present invention will now be described in more detail with further reference to FIG. 2, and with reference to FIGS. 3A–3G, which are flowcharts of the operations performed by the processor or CPU utilized in the device of the present invention.

The basic operations of the device are set forth in FIG. 3A, as follows: operation of the device commences (block 300); the gain of PMT 80 (FIG. 2) is set to zero (block 301 of FIG. 3A); the calibration factor (to be discussed in more detail below) is set to zero (block 302); the PMT unit 34 (FIG. 2) is placed in a "home" position (block 303 of FIG. 3A); the status of the tray 23 (FIG. 1) is checked (block 304 of FIG. 3A); calibration takes place (block 305); and the unit is ready for processing of light intensity data (block 306).

Figures 3A, 3B:
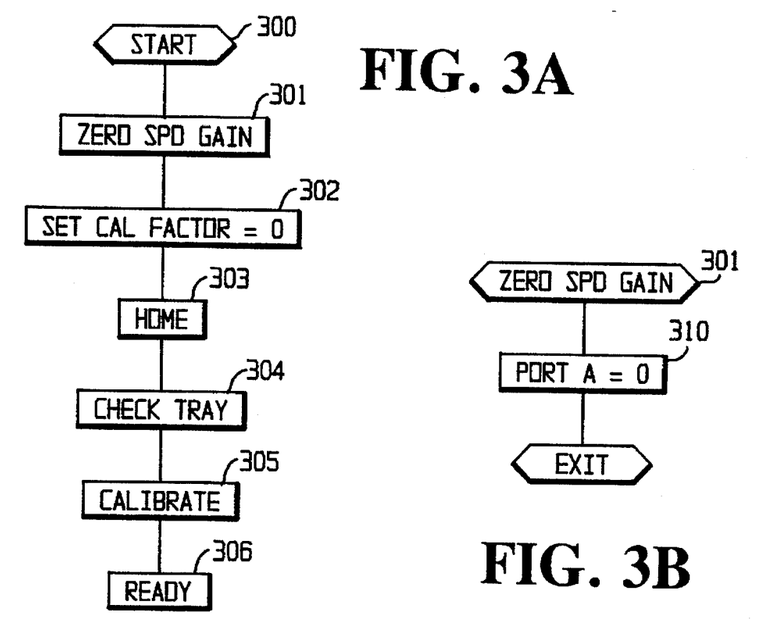
FIGS. 3A-3G are flow charts of the operations performed by the processor or CPU utilized in the device of the present invention.

The operation of block 301 of FIG. 3A is shown in more detail in FIG. 3B. As indicated, zero gain of the PMT unit 34 (FIG. 2) is achieved by setting port A in digital parallel ports 66 of CPU 50 to zero. This results in a zero input to the D/A 72, resulting in a corresponding zero analog output to the PMT 80 and, as a result, the input control voltage VCONT to PMT 80 is set to zero, and the gain of PMT 80 is accordingly set to zero.

In accordance with block 302 of FIG. 3A, the calibration factor (to be discussed in more detail below) of the device of the present invention is set to zero. The operation of block 303 of FIG. 3A is shown in more detail in FIG. 3C.

Figure 3C:
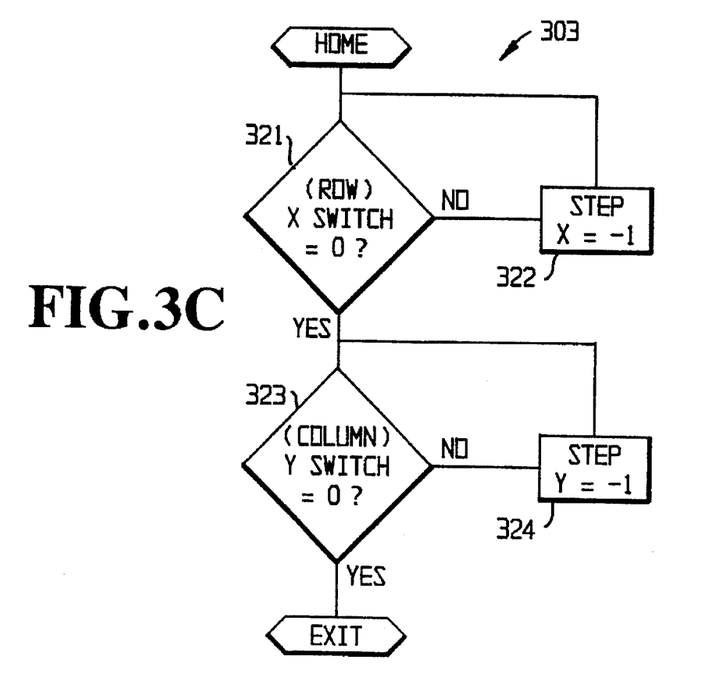

As seen in FIG. 3C, the PMT unit 34 is set to a "home" position, the latter condition being indicated by X-position switch 86 and Y-position switch 88 of PMT unit 34 (see FIG. 2). Specifically, as indicated in FIG. 3C, CPU 50 checks the X-position switch input to digital parallel ports 66 for a zero reading; if zero is not found, CPU 50 provides a drive output signal to X motor driver 76, causing X motor 29 to move the PMT unit 34 one step in the negative X direction, at which point a further check is made, and the process continues until X-position switch 86 indicates a zero reading, indicating that the PMT unit 34 is in an X=0 position. Similarly, as indicated by blocks 323 and 324 of FIG. 3C, CPU 50 makes successive checks of the Y-position switch 88 (FIG. 2), and successively moves the PMT unit 34 in the negative Y direction until a zero reading is obtained, indicating that the PMT trait 34 is in a Y=0 position. When X=0 and Y=0, the PMT unit 34 is in the "home" position.

Figures 3D, 3E, 3G:
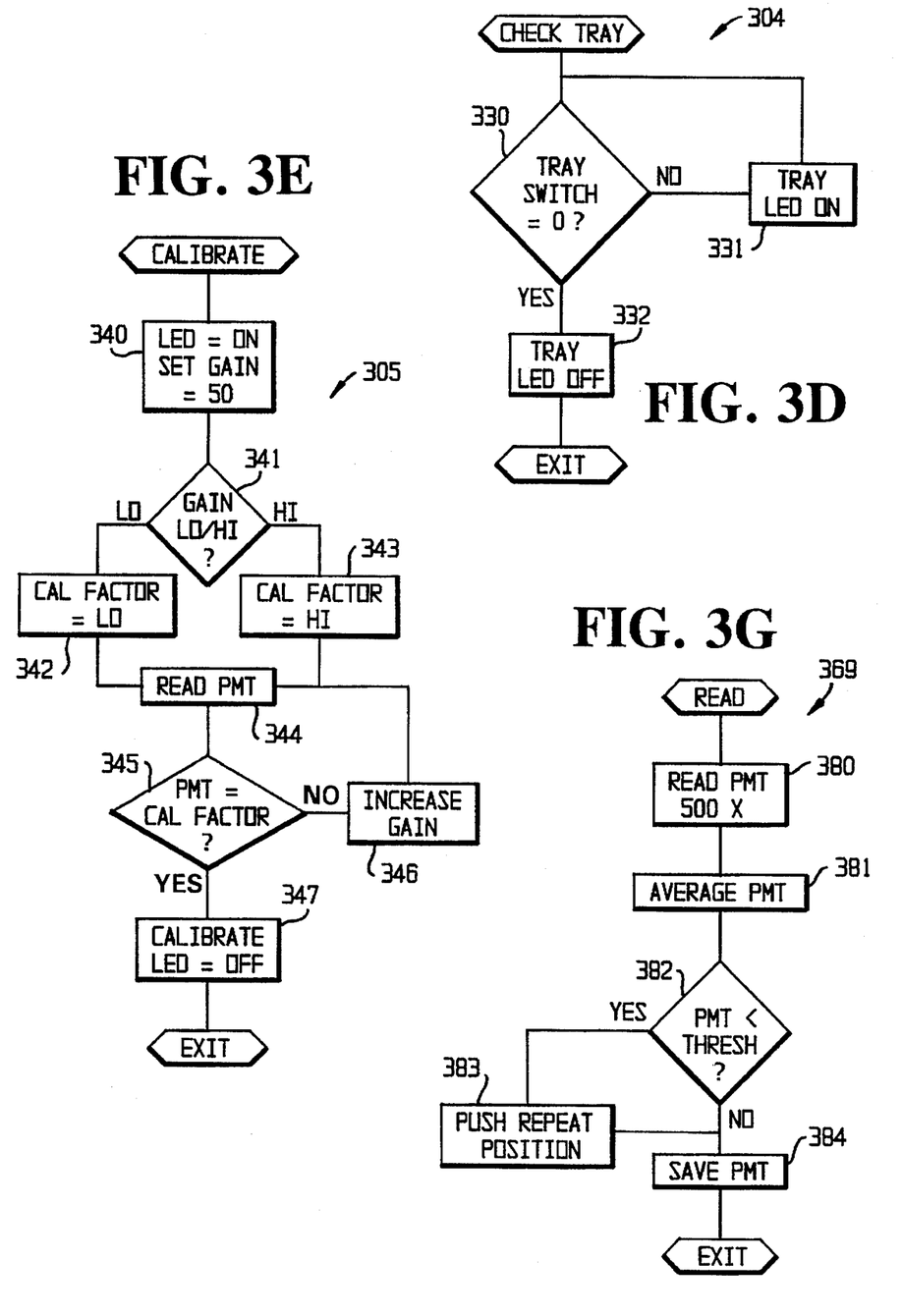

Returning to FIG. 3A, the "check tray" operation of block 304 is shown in more detail in FIG. 3D. Basically, this operation determines when the tray 23 (FIG. 1) has been inserted by the user of the device. When the tray 23 is inserted into the device 10, tray switch 94 (FIG. 2) is closed, and a zero reading is provided by tray switch 94 to the TRAY SWITCH input to digital parallel port 66. As shown in FIG. 2, interface 54 is provided with a tray LED 77a, which is lit so long as the tray is not in position in the device 10 of FIG. 1, but which is turned off (see block 332 of FIG. 3D) once the tray switch 94 gives a zero reading, indicating that the tray 23 (FIG. 1) is in position.

The "calibrate" operation of block 305 of FIG. 3A is shown in more detail in FIG. 3E. Referring back to FIG. 1, it should be noted that mask plate 21 contains, in addition to an array of holes 21a, a further hole 21b corresponding to a calibration position of the PMT unit 34. That is to say, when the PMT unit 34 is in the "home" position (as discussed above with respect to FIG. 3A), it is located above "home" position hole 21b corresponding to a calibration position of PMT unit 34. Beneath the hole 21b in mask plate 21, there is located a calibration LED 93 (shown in FIG. 2 as a component of calibrator/tray detector module 56), and the calibrator LED 93 emits the same light at all times based on its input current supply from constant current supply 92. It should also be recognized, with further reference to FIG. 2, that the current passing through calibration LED 93 is provided, via resistor 95 and connector 96, as an LED CURRENT MONITOR input to the A/D 60 of CPU 50. Once the LED CURRENT MONITOR input is converted to digital form by A/D 60, CPU 50 is able to determine and confirm that the intensity of radiation from calibrator LED 93 is within the proper parameters. Conversely, should the calibrator LED 93 vary substantially in its intensity or even blow out, this will be detected by the CPU 50, and an appropriate indicator to the user of the present invention is provided.

The "calibrate" operation now proceeds for a low gain calibration factor (see blocks 341 and 342 of FIG. 3A). Referring to FIGS. 2 and 3A, CPU 50 provides a ramp function, graduated from 0 to 255 steps in millivolt increments (e.g., 4 mv increments), via digital parallel ports 66 (specifically, port A) and D/A converter 72, to the VCONT input of PMT 80. At each unit of ramp voltage, the output of PMT 80 is read by CPU 50 (block 344). That is, the output of PMT 80 is provided by amplifier 82, low pass filter 84 and connector 90 to the PMT SIGNAL input of A/D converter 60 of CPU 50. In this manner, CPU 50 reads the output of PMT 80 at each ramp step until a "low reading" (blocks 344–346) is reached. At this point, CPU 50 records the step number at which the "low reading" was obtained, and stores that step number. For example, a "low reading" may have been obtained at step 175, so that the step number 175 corresponds to the low gain calibration factor and is stored in memory.

The procedure is then repeated for a high gain calibration factor (blocks 341,343–347). Reading of the PMT 80 continues for subsequent steps until a "high reading" is obtained. For example, a "high reading" may be obtained at step number 210, and that step number corresponds to the high gain calibration factor and is stored in memory. At this point, the PMT unit is fully calibrated.

Figure 3F:
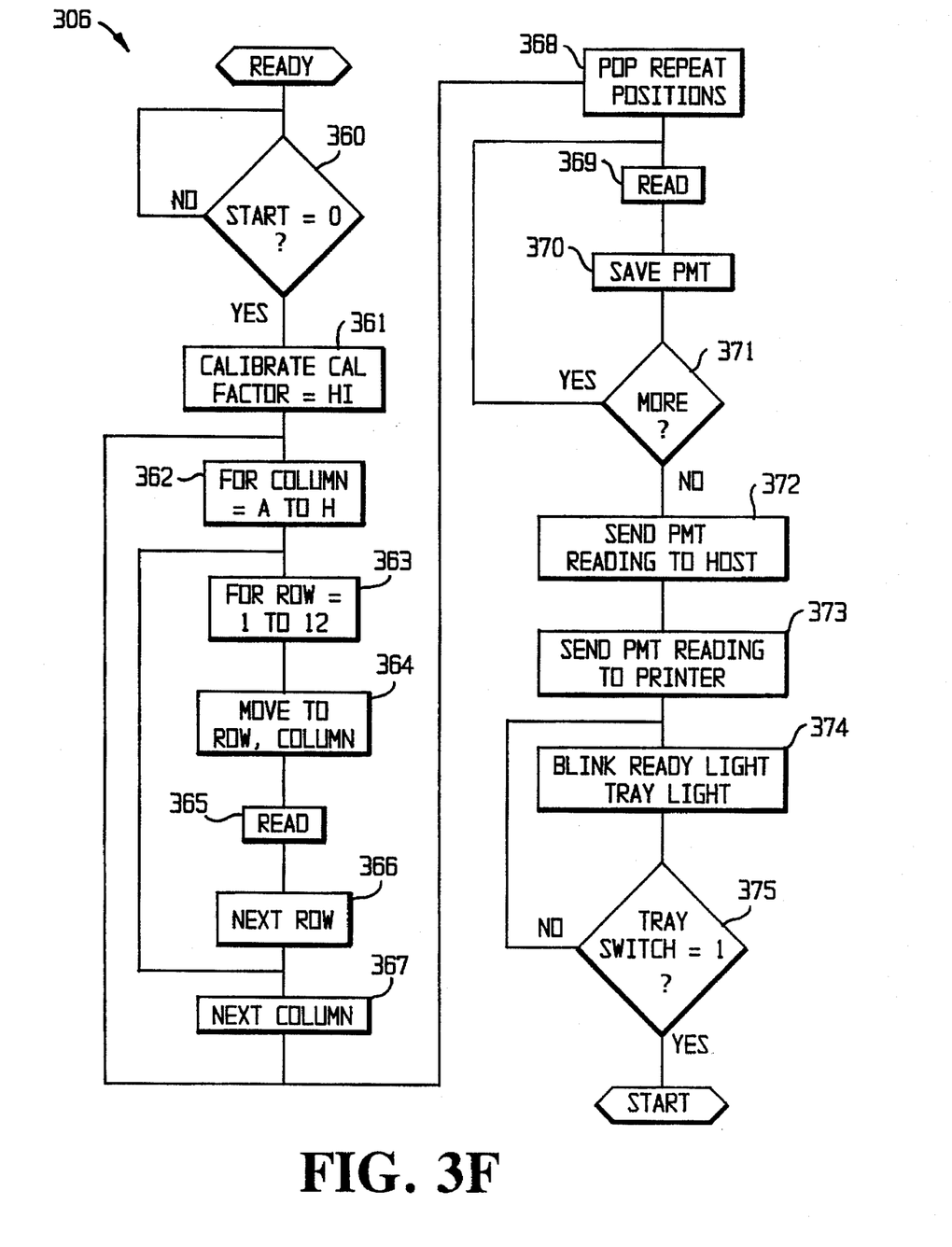

To continue with the description of the operation of the present invention, referring to FIG. 2, CPU 50 forwards the high gain calibration factor from port A of digital parallel ports 66, via D/A converter 72, to the PMT 80 as input control voltage VCONT (see block 361 of FIG. 3F). This represents an improvement over the prior art technique involving adjustment of aperture size, in that provision of the high gain calibration factor in analog form to PMT 80 constitutes a quicker and more reliable adjustment to the "aperture size" of the PMT 80.

The operation of the device of the present invention will be further described with reference to FIGS. 1, 2 and 3F of the drawings (see blocks 362–371 of FIG. 3F). Motors 20 and 29 (FIG. 1) are utilized to drive PMT unit 34 to an initial location (for example, location A1) in the array of wells 21a. Light emanating from the hole at location A1 is detected by PMT 80, and the corresponding analog output thereof is provided, via amplifier 82 and low pass filter 84, to the A/D 60 in CPU 50 where it is converted to digital form and stored in memory as a small n-bit quantity (for example, a 12-bit quantity in a 16-bit storage location).

Then, motor 29 moves PMT 80 to each successive location (A2, A3, and so forth) where light detection is performed and a corresponding n-bit quantity is stored. At the end of a given row in the array of wells 21a, Y-motor 20 moves PMT unit 34 to the next successive row of wells, detection takes place, and X-motor 29 proceeds to move the PMT unit 34 to each successive well in the row in question.

Once the entire array of wells 21a has undergone the detection process, CPU 50 performs a "second pass" through the stored data to see if any value of light emanating from any well is "clipped" or "maxed out". In the latter regard, since the initial data were stored in 12-bit locations, a maximum value of light intensity of $2^n$ is only possible. Thus, if light intensity greater than that value is detected, a low gain factor must be employed to determine the hue value of detected light intensity. In each case where this higher level of light intensity is detected, CPU 50 causes motors 20 and/or 29 to move PMT unit 34 to the corresponding location in the array of wells 21 a, PMT 80 performs another light detection operation, but this time in accordance with a low gain factor, so that the true light intensity value is detected by PMT 80, and is forwarded via amplifier 82 and filter 84 to the A/D converter 60, whereupon the resultant light intensity is converted with a gain factor and stored by CPU 50 in digital form as a 16-bit integer value.

Once CPU 50 performs this "second pass" through the stored data, it causes PMT unit 34 to return to its "home" position. Then, CPU 50 provides a printed output via printer port 64, and/or makes the data available to the user (i.e., a user personal computer) via user interface 62 (see blocks 372 and 373 of FIG. 3F). In addition, CPU 50 issues a control output, via the OUT port of digital parallel ports 66, to the LED's 77a and 77b so as to cause blinking thereof, thereby alerting the user of the completion of the process and of the need for removal of the tray 23 (FIG. 1).

Referring to FIG. 3G, it should be noted that, on each performance of a "read" operation (as indicated in block 369 of FIG. 3F), a plurality of samples (for example, 500 samples—see block 380 of FIG. 3G) is "read" by the A/D converter 60 of CPU 50, and the plurality of samples are then averaged by CPU 50 (see block 381) to obtain the final value of light intensity stored in digital form by CPU 50.

Further referring to FIG. 2, a reset switch 98 is provided in interface 54 for the purpose of canceling present operations in the event that a power fluctuation or other condition necessitates reinitialization of the device.

It should be further noted that PMT 80 in PMT trait 34 provides a reference voltage output VREF to reference circuit 74 in interface 54, and the latter provides a reference voltage (for example, 1.2 volts) to the D/A converter 72, which uses the reference voltage to perform its D/A conversion. Moreover, the voltage control output VCONT of D/A converter 72 is not only provided to the PMT 80, but also is provided as a feedback input REF VOLT MONITOR to the A/D converter 60. This enables the CPU 50 to monitor the input control voltage provided by D/A converter 72 to the PMT 80.

It should be noted that the user interface port 62 in CPU 50 is any conventional serial port (for example, an RS 232 port) for interfacing the CPU 50 to a host or user computer (for example, a personal computer or other work station).

While preferred forms and arrangements have been shown in illustrating the invention, it is to be understood that various changes and modifications may be made without departing from the spirit and scope of this disclosure.

I claim:

1. A device for the detection of light emitted by chemically reactive substances, comprising:

well means comprising a plurality of wells arranged in an array of rows and columns along two axes for holding the chemically reactive substances;

movable detector means for detecting the light emitted by the chemically reactive substance held in each well when said movable detector means is positioned in a respective detection position proximate to each well;

holding means for holding said plurality of wells in a stationary position; and moving means for moving said movable detector means along both of said axes to each respective detection position proximate to each well so as to enable said movable detector means to detect the light emitted by the chemically reactive substance in each well.

2. The device of claims 1, wherein said moving means moves said movable detector means in sequence to each respective detection position corresponding to each well in a given row of said array, and wherein said moving means then moves said movable detector means to each respective detection position corresponding to each well in a next row adjacent to said given row of said array.

3. The device of claim 1, wherein said moving means moves said movable detector means in sequence to each respective detection position corresponding to each well in a given column of said array, and wherein said moving means then moves said movable detector means to each respective detection position corresponding to each well in a next column adjacent to said given column of said array.

4. The device of claim 1, said device further comprising control means for controlling the operation of said moving means.

5. The device of claim 4, wherein said moving means comprises an X-drive motor and Y-drive motor.

6. The device of claim 5, wherein said control means comprises a processor.

7. The device of claim 6, wherein said processor is connected to said movable detector means, said movable detector means providing light detection signals to said processor, and said processor processing said light detection signals to develop light detection data.

8. The device of claim 4, wherein said control means comprises a processor.

9. The device of claim 8, wherein said processor is connected to said movable detector means, said movable detector means providing light detection signals to said processor, and said processor processing said light detection signals to develop light detection dam.

10. The device of claim 4, wherein said movable detector means comprises a photomultiplier tube.

11. The device of claim 10, wherein said photomultiplier tube has a gain, said control means being connected to said photomultiplier tube for controlling the gain thereof.

12. A device for the detection of light emitted by chemically reactive substances, comprising:

well means comprising a plurality of wells for holding the chemically reactive substances;

detector means for detecting the light emitted by the chemically reactive substance held in each well when said detector means is positioned in a respective detection position proximate to each well so as to develop light detection data; and moving means for moving said detector means sequentially to each respective detection position proximate to each well so as to enable said detector means to detect the light emitted by the chemically reactive substance in each well;

wherein said detector means comprises a photomultiplier tube having a gain, said device further comprising control means connected to said photomultiplier tube and responsive to said light detection data for controlling the gain of said photomultiplier tube.

13. The device of claim 1, wherein said detector means produces detection data, said device further comprising processor means connected to said detector means for receiving and processing said detection data.

14. The device of claim 1, further comprising calibrating means for calibrating said detector means to obtain at least one of a high gain calibration factor and a low gain calibration factor.

15. The device of claim 14, wherein said detector means comprises a photomultiplier tube having a gain, and wherein said calibrating means provides said at least one of a high gain calibration factor and a low gain calibration factor as an input control voltage to said photomultiplier tube to adjust the gain thereof.

16. A device for the detection of light emitted by chemically reactive substances, comprising:

well means comprising a plurality of wells for holding the chemically reactive substances;

detector means for detecting the light emitted by the chemically reactive substance held in each well when said detector means is positioned in a respective detection position proximate to each well; and moving means for moving said detector means sequentially to each respective detection position proximate to each well so as to enable said detector means to detect the light emitted by the chemically reactive substance in each well;

wherein said detector means is movable to a calibration position, said device further comprising a calibration light source located at said calibration position, whereby said detector means detects light of known characteristic from said calibration light source and is thereby calibrated when in said calibration position.

17. The device of claim 16, further comprising switch means associated with said detector means for generating an indicator signal when said detector means is in said calibration position.

18. A method for the detection of light emitted by chemically reactive substances, comprising the steps of:

(a) providing a plurality of wells for holding the chemically reactive substances;

(b) providing a detector set to a high gain calibration factor for detecting light emitted by the chemically reactive substances;

(c) moving said detector sequentially to each of a plurality of detection positions proximate to each of the plurality of wells, respectively;

(d) deriving light detection data from light detected at each detection position;

(e) examining said light detection data to determine detection positions for which light detected is clipped;

(f) resetting said detector to a low gain calibration factor; and (g) moving said detector to each detection position determined in step (e) so as to obtain light detection data from light detected at each such detection position based on the low gain calibration factor.

19. A method for the detection of light emitted by chemically reactive substances, comprising the steps of:

(a) providing a plurality of wells for holding the chemically reactive substances;

(b) providing a detector comprising a photomultiplier tube characterized by a gain for detecting light emitted by the chemically reactive substances;

(c) calibrating said photomultiplier tube;

(d) moving said detector sequentially to each of a plurality of detection positions proximate to each of the plurality of wells, respectively; and (e) obtaining light detection data from light detected at each detection position;

wherein step (c) comprises applying successively incremented steps of ramp voltage to said photomultiplier tube, reading an output of said photomultiplier tube for each step of ramp voltage until a low reading is reached, and recording a step number for the step of ramp voltage at which said low reading was reached, whereby a low gain calibration factor is obtained.

20. A method for the detection of light emitted by chemically reactive substances, comprising the steps of:

(a) providing a plurality of wells for holding the chemically reactive substances;

(b) providing a detector comprising a photomultiplier tube characterized by a gain for detecting light emitted by the chemically reactive substances;

(c) calibrating said photomultiplier tube;

(d) moving said detector sequentially to each of a plurality of detection positions proximate to each of the plurality of wells, respectively; and (e) obtaining light detection data from light detected at each detection position;

wherein step (c) further comprises applying successively incremented steps of ramp voltage to said photomultiplier tube, reading an output of said photomultiplier tube for each step of ramp voltage until a high reading is reached, and recording a step number for the step of ramp voltage at which said high reading was reached, whereby a high gain calibration factor is obtained.

* * * * *